(12) United States Patent
Rousseau et al.

(10) Patent No.: US 12,349,723 B2
(45) Date of Patent: *Jul. 8, 2025

(54) COCOA WRAPPER FOR SMOKING ARTICLES

(71) Applicant: Mativ Holdings, Inc., Alpharetta, GA (US)

(72) Inventors: Cedric Rousseau, Le Mans (FR); Jerome Accou, Le Mans (FR); Arthur Gouth, Le Mans (FR); Laurent Gombert, Le Mans (FR)

(73) Assignee: SWM Holdings US, LLC, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/355,037

(22) Filed: Jul. 19, 2023

(65) Prior Publication Data

US 2023/0363443 A1     Nov. 16, 2023

Related U.S. Application Data

(63) Continuation of application No. 16/788,105, filed on Feb. 11, 2020, now Pat. No. 11,723,398.

(Continued)

(51) Int. Cl.
*A24D 1/02* (2006.01)
*A24D 1/00* (2020.01)
(Continued)

(52) U.S. Cl.
CPC .............. *A24D 1/02* (2013.01); *A24D 1/002* (2013.01); *A24D 1/022* (2013.01); *A24D 1/025* (2013.01); *A61K 31/05* (2013.01); *A61K 31/352* (2013.01)

(58) Field of Classification Search
CPC .......... A24D 1/02; A24D 1/025; A24D 1/002; A24D 1/022
See application file for complete search history.

(56) References Cited

U.S. PATENT DOCUMENTS

| | | |
|---|---|---|
| 2,418,296 A | 4/1947 | Frederickson |
| 3,012,914 A | 12/1961 | Battista et al. |

(Continued)

FOREIGN PATENT DOCUMENTS

| | | |
|---|---|---|
| CN | 1179922 | 4/1998 |
| CN | 101886355 | 11/2010 |

(Continued)

OTHER PUBLICATIONS

"Extraction", Cambridge Dictionary, https://dictionary.cambridge.org/us/dictionary/english/extraction, Accesed Aug. 9, 2024 (Year: 2024).*

(Continued)

*Primary Examiner* — Michael H. Wilson
*Assistant Examiner* — Stephanie Lynn Moore
(74) *Attorney, Agent, or Firm* — Dority & Manning, P.A.

(57) ABSTRACT

A wrapping material for a smoking article is formed from a web that includes extracted pieces of cocoa husk combined with web building fibers. The web has a basis weight of from about 20 gsm to about 80 gsm and a permeability of from about 10 Coresta to about 100 Coresta. The wrapping material has a pleasant and neutral smell and taste. The wrapping material is tobacco and nicotine free and can be used as a carrier for flavorings or aerosol delivery agents.

22 Claims, 3 Drawing Sheets

Related U.S. Application Data

(60) Provisional application No. 62/857,595, filed on Jun. 5, 2019, provisional application No. 62/803,815, filed on Feb. 11, 2019.

(51) Int. Cl.
*A61K 31/05* (2006.01)
*A61K 31/352* (2006.01)

(56) References Cited

U.S. PATENT DOCUMENTS

| | | | |
|---|---|---|---|
| 3,100,492 A | 8/1963 | Schmidt | |
| 3,203,432 A | 8/1965 | Green et al. | |
| 3,429,316 A * | 2/1969 | Hess | A24B 15/16 131/359 |
| 3,943,942 A * | 3/1976 | Anderson | A24B 15/16 131/359 |
| 4,201,228 A | 5/1980 | Lewinger | |
| 4,279,824 A | 7/1981 | McKinney | |
| 4,459,998 A | 7/1984 | Labbe | |
| 4,681,126 A | 7/1987 | Strubel et al. | |
| 4,719,929 A | 1/1988 | Breckwoldt | |
| 4,813,438 A | 3/1989 | Fleming | |
| 4,969,477 A | 11/1990 | Yagisawa | |
| 4,987,906 A | 1/1991 | Young et al. | |
| 5,119,836 A | 6/1992 | White | |
| 5,135,010 A | 8/1992 | Fan | |
| 5,143,097 A | 9/1992 | Stephen Sohn et al. | |
| 5,159,942 A | 11/1992 | Brinkley et al. | |
| 5,203,355 A | 4/1993 | Clearman et al. | |
| 5,322,076 A | 6/1994 | Brinkley et al. | |
| 5,323,791 A | 6/1994 | Wu et al. | |
| 5,325,877 A | 7/1994 | Young et al. | |
| 5,339,838 A | 8/1994 | Young et al. | |
| 5,377,698 A | 1/1995 | Litzinger et al. | |
| 5,501,237 A | 3/1996 | Young et al. | |
| 5,513,663 A | 5/1996 | Van Leuven et al. | |
| 5,533,530 A | 7/1996 | Young et al. | |
| 5,562,108 A | 10/1996 | Hardy et al. | |
| 5,715,844 A | 2/1998 | Young et al. | |
| 5,908,034 A | 6/1999 | Adedeji | |
| 6,289,897 B1 | 9/2001 | McAdam et al. | |
| 6,679,270 B2 | 1/2004 | Baskevitch et al. | |
| 6,699,288 B2 | 3/2004 | Moret | |
| 6,929,013 B2 | 8/2005 | Ashcraft et al. | |
| 7,323,197 B1 | 1/2008 | Lukacs | |
| 7,428,905 B2 | 9/2008 | Mua | |
| 7,836,896 B2 | 11/2010 | Nadimi | |
| 8,047,209 B2 | 11/2011 | May | |
| 8,469,038 B2 | 6/2013 | Sinclair, Jr. | |
| 8,646,461 B2 | 2/2014 | Von Bostel et al. | |
| 8,813,760 B2 | 8/2014 | May, Jr. | |
| 8,897,628 B2 | 11/2014 | Conley et al. | |
| 9,022,041 B2 | 5/2015 | Marsi | |
| 9,095,173 B2 | 8/2015 | Sinclair, Jr. | |
| 9,220,298 B1 | 12/2015 | En'Wezoh et al. | |
| 9,428,757 B2 | 8/2016 | Senger et al. | |
| 9,433,240 B2 | 9/2016 | Sinclair, Jr. | |
| 9,462,829 B2 | 10/2016 | Van Den Berg | |
| 9,474,725 B1 | 10/2016 | Reillo et al. | |
| 9,532,593 B2 | 1/2017 | Turner | |
| 9,655,381 B2 | 5/2017 | Sinclair, Jr. | |
| 9,675,103 B2 | 6/2017 | Sinclair, Jr. | |
| 9,839,612 B2 | 12/2017 | Reillo et al. | |
| 9,950,858 B2 | 4/2018 | Byrd, Jr. et al. | |
| 9,956,911 B2 | 5/2018 | Wright | |
| 9,972,680 B2 | 5/2018 | Reillo et al. | |
| 9,974,739 B2 | 5/2018 | Reillo et al. | |
| 10,016,360 B1 | 7/2018 | Elbogen et al. | |
| 10,076,135 B2 | 9/2018 | Lisauskas et al. | |
| 10,080,385 B2 | 9/2018 | Sinclair | |
| 10,165,795 B2 | 1/2019 | O'Malley | |
| 10,172,897 B2 | 1/2019 | Vu et al. | |
| 10,178,872 B2 | 1/2019 | Mompon | |
| 10,206,427 B2 | 2/2019 | Pijnenberg et al. | |
| 10,226,066 B2 | 3/2019 | Moldoveanu et al. | |
| 10,271,578 B2 | 4/2019 | John et al. | |
| 10,639,439 B2 | 5/2020 | Larson | |
| 10,729,662 B2 | 8/2020 | Ragot et al. | |
| 10,750,773 B2 | 8/2020 | Yang et al. | |
| 11,723,398 B2 * | 8/2023 | Rousseau | A61K 31/352 131/335 |
| 2003/0131860 A1 | 7/2003 | Ashcraft et al. | |
| 2004/0099280 A1 * | 5/2004 | Stokes | A24D 1/025 131/365 |
| 2004/0103908 A1 | 6/2004 | Prakash et al. | |
| 2005/0263165 A1 | 12/2005 | Oh et al. | |
| 2006/0021626 A1 | 3/2006 | Mua | |
| 2008/0000488 A1 | 1/2008 | Nadimi et al. | |
| 2009/0050165 A1 | 2/2009 | Murali | |
| 2009/0120450 A1 | 5/2009 | Herve et al. | |
| 2012/0095088 A1 | 4/2012 | Hospodor | |
| 2012/0152264 A1 | 6/2012 | Coleman et al. | |
| 2012/0318286 A1 | 12/2012 | Lisauskas et al. | |
| 2014/0166028 A1 | 6/2014 | Fuisz et al. | |
| 2014/0216481 A1 | 8/2014 | Freeman | |
| 2014/0295049 A1 | 10/2014 | Ragot et al. | |
| 2014/0360520 A1 | 12/2014 | May | |
| 2015/0037389 A1 | 2/2015 | Ragot et al. | |
| 2015/0068544 A1 | 3/2015 | Moldoveanu et al. | |
| 2015/0083142 A1 | 3/2015 | Sinclair, Jr. | |
| 2015/0107614 A1 | 4/2015 | Sinclair, Jr. | |
| 2015/0374030 A1 | 12/2015 | Lisauskas et al. | |
| 2016/0029690 A1 | 2/2016 | Sinclair | |
| 2016/0037823 A1 | 2/2016 | Ruben | |
| 2016/0193266 A1 | 7/2016 | Ablett | |
| 2016/0208440 A1 * | 7/2016 | Byrd, Jr. | B65D 85/1045 |
| 2016/0213057 A1 * | 7/2016 | Goldoni, Jr. | D21H 19/20 |
| 2016/0255854 A1 | 9/2016 | Rousseau | |
| 2016/0302474 A1 | 10/2016 | Chen et al. | |
| 2016/0366926 A1 | 12/2016 | Uren | |
| 2017/0035095 A1 | 2/2017 | Zuchuat et al. | |
| 2017/0112187 A1 | 4/2017 | Ostrander | |
| 2017/0112188 A1 | 4/2017 | Ostrander | |
| 2017/0112189 A1 | 4/2017 | Stern | |
| 2017/0119039 A1 | 5/2017 | Dena et al. | |
| 2017/0172201 A1 | 6/2017 | Turner | |
| 2017/0174404 A1 | 6/2017 | Ragot et al. | |
| 2017/0181466 A1 | 6/2017 | Batista | |
| 2017/0188623 A1 | 7/2017 | Cranford | |
| 2017/0202895 A1 | 7/2017 | Hugh | |
| 2017/0202896 A1 | 7/2017 | Hugh | |
| 2017/0245542 A1 | 8/2017 | Zappoli | |
| 2017/0258128 A1 | 9/2017 | Lisauskas et al. | |
| 2017/0273347 A1 | 9/2017 | Klipfel et al. | |
| 2017/0273349 A1 | 9/2017 | Moore | |
| 2017/0303576 A1 | 10/2017 | Rousseau | |
| 2017/0333503 A1 | 11/2017 | Ayres | |
| 2017/0347699 A1 | 12/2017 | Sinclair, Jr. | |
| 2018/0027869 A1 | 2/2018 | Scott | |
| 2018/0116276 A1 | 5/2018 | Prog et al. | |
| 2018/0137792 A1 | 5/2018 | Gransaull | |
| 2018/0168224 A1 | 6/2018 | Naughton et al. | |
| 2018/0213838 A1 | 8/2018 | Richmond et al. | |
| 2018/0233558 A1 | 8/2018 | Reillo et al. | |
| 2018/0271826 A1 | 9/2018 | Sievers et al. | |
| 2018/0279666 A1 | 10/2018 | Aoun et al. | |
| 2018/0325972 A1 | 11/2018 | Moore | |
| 2018/0344790 A1 | 12/2018 | Vu et al. | |
| 2018/0352848 A1 | 12/2018 | Vu et al. | |
| 2018/0360099 A1 | 12/2018 | Ibrahim | |
| 2018/0360103 A1 | 12/2018 | Kaplan et al. | |
| 2019/0022158 A1 | 1/2019 | Greenbaum et al. | |
| 2019/0145050 A1 | 5/2019 | Rousseau et al. | |
| 2019/0262304 A1 | 8/2019 | Townsend et al. | |
| 2019/0380377 A1 | 12/2019 | Rabes | |
| 2020/0101013 A1 | 4/2020 | Ragot et al. | |
| 2020/0108018 A1 | 4/2020 | Shadurin et al. | |
| 2020/0179269 A1 | 6/2020 | Tamir et al. | |
| 2020/0197639 A1 | 6/2020 | Larson | |
| 2020/0205463 A1 | 7/2020 | Lamblin | |
| 2020/0253264 A1 | 8/2020 | Rousseau et al. | |
| 2020/0253266 A1 | 8/2020 | Rousseau et al. | |

(56) References Cited

U.S. PATENT DOCUMENTS

| | | | |
|---|---|---|---|
| 2020/0253268 A1 | 8/2020 | Rousseau et al. | |
| 2020/0253269 A1 | 8/2020 | Rousseau et al. | |
| 2020/0275688 A1 | 9/2020 | Rousseau | |
| 2020/0297023 A1 | 9/2020 | Billon et al. | |

FOREIGN PATENT DOCUMENTS

| | | |
|---|---|---|
| CN | 103161091 | 6/2013 |
| CN | 103704882 | 4/2014 |
| EP | 0336458 | 10/1989 |
| EP | 0337506 | 10/1989 |
| EP | 0339689 | 11/1989 |
| EP | 0271036 | 3/1992 |
| EP | 1797779 | 6/2006 |
| EP | 1420659 | 6/2007 |
| IN | 3540DEL2012 | 12/2012 |
| WO | WO2002047494 | 6/2002 |
| WO | WO2003020057 | 3/2003 |
| WO | WO2004043173 | 5/2004 |
| WO | WO2004047572 | 6/2004 |
| WO | WO2004068974 | 8/2004 |
| WO | WO2006097447 | 9/2006 |
| WO | WO2011127679 | 10/2011 |
| WO | WO2011127680 | 10/2011 |
| WO | WO2014106819 | 7/2014 |
| WO | WO2016026810 | 2/2016 |
| WO | WO2016050873 | 4/2016 |
| WO | WO2016171997 | 10/2016 |
| WO | WO2017174661 | 10/2017 |
| WO | WO2018143952 | 8/2018 |
| WO | WO2018178978 | 10/2018 |
| WO | WO2020/097430 | 5/2020 |

OTHER PUBLICATIONS

Co pending U.S. Appl. No. 16/998,514, filed Aug. 20, 2020.
Chinese Office Action Corresponding to Application No. 202080026609.X on Mar. 1, 2023.

* cited by examiner

COCOA WRAPPER FOR SMOKING ARTICLES

RELATED APPLICATIONS

The present application is based on and claims priority to U.S. patent application Ser. No. 16/788,105, filed on Feb. 11, 2020, which is based on and claims priority to U.S. Provisional Patent Application Ser. No. 62/857,595, filed on Jun. 5, 2019 and U.S. Provisional Patent Application Ser. No. 62/803,815, filed on Feb. 11, 2019, all of which are incorporated herein by reference.

BACKGROUND

Smoking articles, such as cigarettes or little cigars, are conventionally made by wrapping a column of filler in a wrapping material, made of cigarette paper or homogenized tobacco. At one end, the smoking article usually includes a filter or a tip through which the article is smoked.

It has long been recognized in the industry that wrappers for smoking articles have a significant influence on the smoking characteristics of smoking articles. In this regard, various attempts have been made in the art to alter or modify wrappers for smoking articles in order to achieve a wrapper that improves the overall smoking experience of the smoking article. Wrapping papers for smoking articles were typically formed from pulp fibers, such as wood or flax fibers, combined with filler particles. However, such wrapping papers often produced a "papery" taste that was regarded as unpleasant by the user.

Furthermore, pulp fibers are mainly composed of delignified fibers from hardwood and softwood trees, raising concerns regarding the sustainability of a wrapper mainly formed from pulp fibers due to the large reliance upon felled trees. Specifically, between two and three tons of wood are required to manufacture one ton of conventional paper. Furthermore, since 1950, the worldwide consumption of paper has drastically increased. This increase in consumption has an impact on the forests of the planet, 80% of which would have disappeared as a result of human activity.

Wrapping homogenized tobacco materials, on the other hand, were typically made of processed tobacco by-products in an amount greater than 50% and could not achieve satisfying ash appearance or combustibility, and also contain high amounts of tobacco by-products. One component or chemical contained in conventional tobacco leaves is nicotine. Nicotine, however, can have an addictive effect on certain users depending upon the concentration of deliveries. Due to its addictive effect, various rulemaking bodies and the tobacco industry have attempted to produce smoking articles with reduced nicotine levels.

In view of the above, a need currently exists for a wrapper for a smoking article that has a pleasant or neutral taste. Similarly, a need exists to provide a wrapper for a smoking article that has adequate burn properties in addition to having a pleasant or neutral taste. It would also be beneficial to provide a wrapper for a smoking article that has improved smoking characteristics and that is free from nicotine. Furthermore, it would be beneficial to provide a smoking article that has improved smoking characteristics and that may also serve as a carrier for one or more additives. Moreover, it would be an advantage to provide a wrapper that is at least partially formed from a sustainable source. Additionally, it would be beneficial to produce a smoking article with a differentiating visual aspect. Finally, it would also be an advantage to form a wrapper that, while being tobacco and/or nicotine free itself, may serve as a carrier for aerosol delivery agents.

SUMMARY

It is to be understood by one of ordinary skill in the art that the present discussion is a description of exemplary embodiments only, and is not intended as limiting the broader aspects of the present disclosure.

Generally, the present disclosure is directed to a wrapping material (that may also be referred to as a web, or being formed from a web herein) for a smoking article that includes a web. The web includes extracted cocoa husk fibers combined with web building fibers, where the web building fibers include delignified cellulosic fibers. The web has a basis weight of from about 20 gsm to about 80 gsm, and a permeability of from about 10 Coresta to about 100 Coresta.

In one embodiment, the extracted cocoa husk fibers are combined with the web building fibers in a manner that produces a uniform speckled appearance over a surface of the wrapping material.

Additionally or alternatively, the web includes a filler combined with the extracted cocoa husk and the web building fibers. In an embodiment that includes a filler, the filler may be included in the web in an amount of from about 0% to about 40% by weight, preferably from about 5% to about 20% by weight, and even more preferably in an amount from 10% to about 20% by weight of the wrapping material. In a further embodiment, the filler includes calcium carbonate particles, titanium dioxide particles, kaolin particles, talc particles, barium sulfate particles, bentonite particles, zeolite particles, silicate particles or mixtures thereof. Moreover, in one embodiment, the filler contained in the wrapper has an average particle size of from about 0.1 microns to about 10 microns.

In yet a further embodiment, the web has a permeability of from about 30 Coresta to about 80 Coresta, such as from about 40 Coresta to about 60 Coresta. Additionally or alternatively, the web can have a basis weight of from about 30 gsm to about 50 gsm. In one embodiment, the web contains the web building fibers in an amount sufficient for the web to have a tensile strength of greater than about 1000 cN/15 mm, such as greater than about 1250 cN/15 mm, such as greater than about 1500 cN/15 mm, and less than about 4000 cN/15 mm when tested according to ASTM Test D828-97.

In one embodiment, the web according to the present disclosure may be calendared.

In another embodiment, the wrapping material includes an aerosol delivery composition applied to the web, and the aerosol delivery composition includes an aerosol delivery agent. In one embodiment, the aerosol delivery agent includes a drug or a flavorant. In yet another embodiment, the aerosol delivery composition comprises an oil or a solid. Furthermore, in an embodiment, the aerosol delivery agent includes nicotine, a cannabinoid, tetrahydrocannabinol, or cannabidiol. In a further embodiment yet, the aerosol delivery agent includes a sugar, a licorice extract, honey, a coffee extract, maple syrup, a tea extract, a plant extract, a botanical extract, a tobacco extract, or a fruit extract. Additionally or alternatively, the aerosol delivery composition is present on the web in an amount greater than about 0.1% by weight, such as greater than about 1% by weight, such as greater than about 5% by weight, such as greater than about 10% by weight, such as greater than about 15% by weight, such as greater than about 20% by weight, such as greater than about 25% by weight, such as greater than about 30% by weight, such as greater than about 35% by weight, and less than about 40% by weight.

In yet a further embodiment, the web contains water soluble cocoa husk components in an amount less than about 10% by weight, such as less than about 8% by weight. Alternatively, the web contains water soluble cocoa husks components in an amount greater than about, 10% by weight, such as about 15% by weight or greater, such as about 20% by weight or greater, such as about 25% by weight or greater, such as up to about 30% by weight.

Additionally or alternatively, in one embodiment, the web building fibers include softwood fibers. In a further embodiment, the web building fibers include flax fibers, hemp fibers, abaca fibers, wood pulp fibers, bamboo fibers, coconut fibers, ramie fibers, jute fibers, or mixtures thereof. In one embodiment, the web building fibers are present in the web in an amount greater than about 20% by weight, such as in an amount greater than about 30% by weight, such as in an amount greater than about 40% by weight, and in an amount less than about 80% by weight.

In a further embodiment, the wrapping material is tobacco-free.

In yet another embodiment, the web has been treated with a burn control agent. In a further embodiment, the burn control agent comprises a salt of a carboxylic acid, such as a citrate or a succinate, the burn control agent being present in the web in an amount of from about 0.1% by weight to about 5% by weight, such as in an amount from about 1% by weight to about 3% by weight.

Furthermore, in an embodiment, the web has been treated with a humectant. In an additional embodiment, the humectant includes glycerol, propylene glycol, or mixtures thereof.

Additionally or alternatively, in one embodiment, the web is treated with a gum. In one embodiment, the gum includes guar gum, alginate, cellulose, cellulose derivatives such as carboxymethyl cellulose, arabic gum, or mixtures thereof. In one embodiment, the gum is present on the web in an amount of from about 0.1% by weight to about 5% by weight.

In a further embodiment, the wrapping material includes a plurality of discrete reduced ignition areas spaced along a first direction of the wrapping material, the reduced ignition areas having a diffusivity of less than about 0.5 cm/s at 23° C. In one embodiment, the plurality of reduced ignition areas are formed by applying a reduced ignition composition to the web.

In general, the present disclosure is also generally directed to a wrapping material according to the present disclosure incorporated into a smoking article. When the smoking article is tested according to ASTM Test E2187-09, at least 75% of the smoking articles self-extinguish.

Generally speaking, the present disclosure is also directed to a smoking article that includes a smokeable rod surrounded by the wrapping material of the present disclosure.

Other features and aspects of the present disclosure are discussed in greater detail below.

BRIEF DESCRIPTION OF THE DRAWINGS

A full and enabling disclosure of the present disclosure is set forth more particularly in the remainder of the specification, including reference to the accompanying figures, in which.

Figure 1:
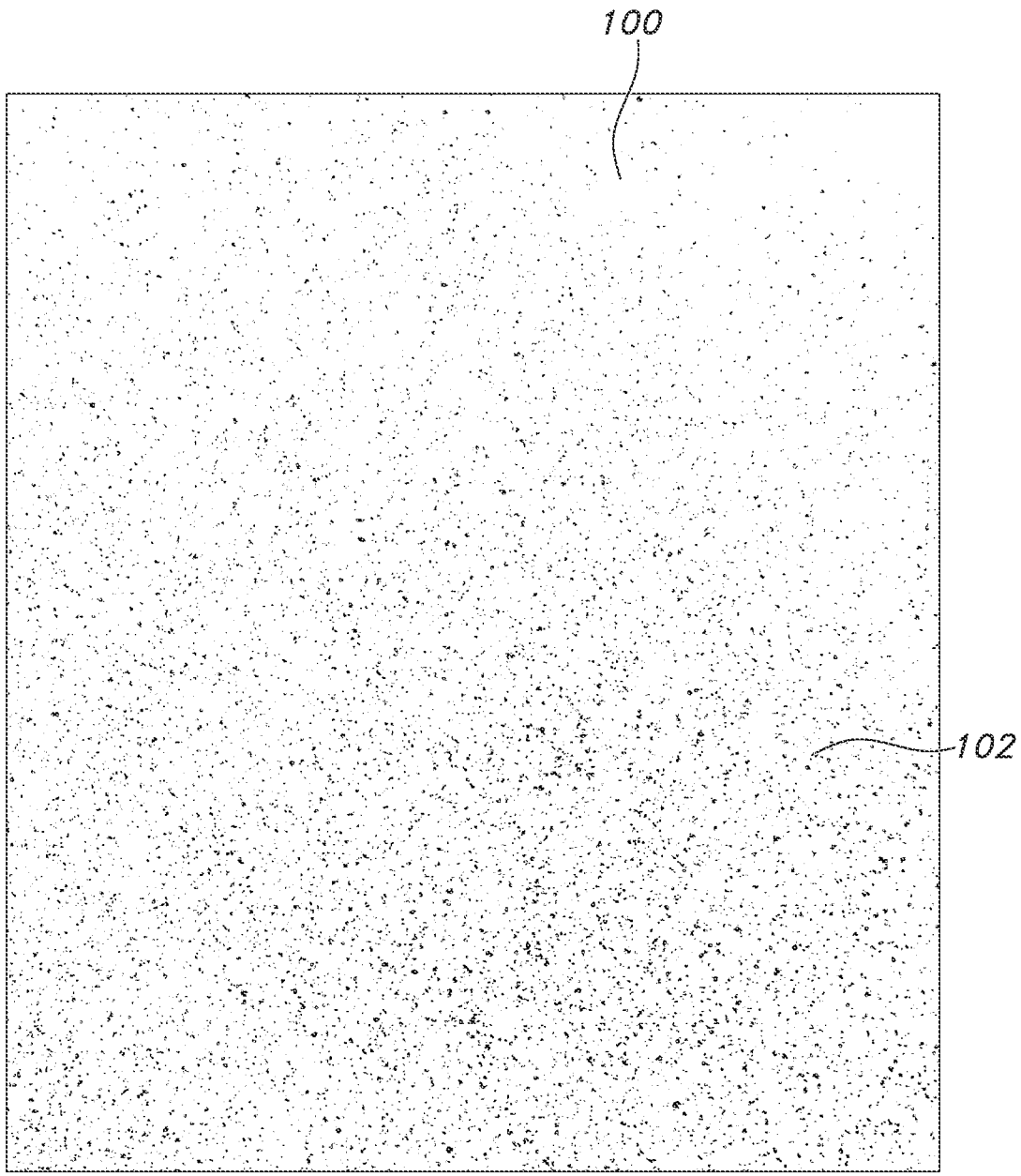
FIG. 1 is a plan view of one embodiment of a wrapping material made in accordance with the present disclosure.

Repeat use of reference characters in the present specification and drawings is intended to represent the same or analogous features or elements of the present invention.

Definitions

As used herein, a "reconstituted plant material" or "reconstituted cocoa material" refers to a material formed by a process in which a plant feed stock, such as cocoa shells, is extracted with a solvent to form an extract of solubles, such as water solubles, and an extracted insoluble portion or residue comprising fibrous material. The extracted and insoluble fibrous material is then formed into a sheet or web through any suitable process and the extract may either be discarded or reapplied to the formed sheet. The extract can be fed through various processes for concentrating the extract and optionally removing or adding various components prior to being recombined with the fibrous material. In the present disclosure, the reconstituted plant material is formed from extracted cocoa husk fibers combined with web building fibers, such as cellulose fibers. The extract of solubles obtained from the cocoa husk fibers is optionally reapplied to the sheet. Therefore, it should be understood that, the wrapping material, web, and/or sheet may all be formed of reconstituted plant material, and may be referred to as such throughout the description.

As used herein, an "aerosol generating material" is meant to include both a combustible material that undergoes combustion in a smoking article and to an aerosol-forming material that is heated but not combusted to form an inhalable aerosol. Combustible smoking articles can include machine-made or hand-made cigarettes, cigarillos and cigars, with or without a filter or a tip. In a cigarette, the aerosol generating material is generally surrounded by a wrapping material to form a smokable rod, but may also be included in the wrapping material itself. Aerosol generating devices for generating an aerosol include, for instance, devices in which an aerosol is generated by electrical heating or by the transfer of heat from a combustible fuel element or heat source to heat but not burn the aerosol generating material, which releases volatile compounds. As the released compounds cool, they condense to form an aerosol that is inhaled by the consumer.

As used herein, "extracted cocoa husk fibers" refers to cocoa husk fibers that have been subjected to an extraction process in which the cocoa husk has been contacted with an aqueous solution to remove greater than 90% of the water soluble components contained in the cocoa husks. The extraction process is different from a delignification process and from a bleaching treatment.

As used herein, "delignified" cellulosic fibers refers to fibers that have been subjected to a pulping or delignification process by which the cellulose fibers are separated from the plant material through chemical means, mechanical means, or through a combination of chemical and mechanical means.

As used herein, "*cannabis*" may refer to any variety of the *Cannabis* plant, such as *Cannabis sativa* or *Cannabis indica*, for instance. More particularly, the present disclosure may refer to leaves, stems, seeds and flowers or any other part of the *Cannabis* plant, as *cannabis*. Nonetheless, *cannabis*, as referred to herein, includes *cannabis* that contains average or high levels of THC and/or CBD (usually known as marijuana), hemp, which may contain low, or very low, levels of THC, industrial hemp, which may refer to a *cannabis* plant that contains less than 0.3% THC, or combinations thereof.

As used herein, the term "refine" is used to mean that the plant material is subjected to a mechanical treatment that modifies the fibers of the material so that they are better suited to forming a fibrous sheet or substrate. Refining can be accomplished using a conical refiner or a disks refiner or a Valley beater. The mechanical process exerts an abrasive and bruising action on the plant material such that the plant material is defibrillated. Refining is a different process than delignification and pulping.

The Freeness value (° SR) measures generally the rate at which a dilute suspension of refined fibers may be drained. The freeness is measured by the Schopper Riegler Method for drainability. As used herein, freeness is measured according to Test NORM EN ISO 5267-1.

As used herein, the "amount of water soluble extracts" present in a substrate or reconstituted plant material or in an aerosol-generating material is determined by taking 5 grams of a sample in boiling distilled water for 10 minutes to obtain an extract containing water soluble components. The weight of dry matter of the extract that is soluble in the solvent is calculated by the difference between the dry weight of the original sample and the dry weight of the sample after extraction. The difference in dry weight is then used to determine the percentage of water soluble extracts in the sample.

DETAILED DESCRIPTION

It is to be understood by one of ordinary skill in the art that the present discussion is a description of exemplary embodiments only, and is not intended as limiting the broader aspects of the present disclosure.

The present disclosure is generally directed to a wrapping material for a smoking article that is formed from a web that includes cocoa husk and web building fibers. In such a manner, the web for the wrapping material according to the present disclosure may be at least partially formed from a sustainable material that would normally become waste as part of the cocoa roasting process. Furthermore, it was unexpectedly found that a web formed from extracted cocoa husks has a pleasant neutral taste and serves as an excellent carrier due to its absorbency properties, even when combined with web building fibers that may include pulp fibers. Moreover, it was found that a wrapping material that is at least partially formed from cocoa husk unexpectedly had good burn characteristics in addition to a pleasant, neutral taste and good carrier properties.

Further, because cocoa has a neutral taste when smoked and is nicotine free, the wrapping material can be used to produce a nicotine free smoking article. In addition, the wrapping material is well suited to being combined with other materials with aerosol delivery functionality and/or topical additives, which may be jointly referred to as aerosol delivery agents and will be discussed in greater detail below. For instance, due to its good carrier properties, the wrapping material may also be combined with an aerosol delivery agent or have an aerosol delivery agent applied thereto.

When combined with a tobacco material, the wrapping material of the present disclosure, due to its neutral characteristics, does not in any way mask the taste of the aerosol delivery agents and, in fact, can enhance the smoking or experience by diluting and decreasing irritants. Moreover, as the aerosol delivery agent is applied after formation of the wrapper in a metered amount, and is not merely an inherent property of the material used to form the wrapper, the amount of the aerosol delivery agent, including the active amount, may be carefully controlled and metered.

As described above, the wrapping material of the present disclosure is generally formed from extracted cocoa husks combined with web building fibers. *Cocoa* materials for use in the present disclosure are obtained from *Theobroma cocoa*, which is also referred to as the cocoa tree. The cocoa tree is in the evergreen family and is native to tropical regions. The cocoa tree produces a fruit, referred to as a cocoa pod. *Cocoa* pods are generally yellow to orange in color and can weight over one pound when ripe. The pod contains anywhere from 10 to about 80 cocoa beans that are used to produce chocolate, juices, jelly, and the like. After the beans are removed from the cocoa pod, the cocoa beans are dried and cured by being exposed to sunlight and/or ultraviolet light. Each individual bean is covered in a husk or shell. The husk or shell is removed from the bean prior to using the bean for producing food products. The wrapping material of the present disclosure is made from the cocoa shells or husks, although other components of the cocoa pod may also be used.

Previously, it was believed that fibers from cocoa shells were not well suited to producing web materials, as the fibers produced a web that had inadequate strength and basis weight to form wrapping materials or to be used in machines for forming wrapping materials. However, the present disclosure has found that, by selectively forming a web according to the present disclosure, cocoa husk may be used to form a wrapping material.

In one embodiment, the cocoa husks are optionally sized or ground and then subjected to an extraction process for removing water soluble components. The extracted cocoa husks can then be combined with web building fibers and formed into a substrate, such as a reconstituted sheet. The substrate can optionally be treated with the extract obtained from the cocoa husks. Alternatively, the extract obtained from the cocoa husks can be discarded and not recombined with the water insoluble fibers and other materials. The reconstituted material is then dried and formed into a web and/or a wrapping material. The web and/or a wrapping material can then optionally be combined with various other components. For instance, the wrapping material can be treated with various aerosol delivery agents and/or combined, either during or after the initial refining process, with various other aerosol delivery compounds, such as tobacco materials or other herbal fillers, such that the wrapping material itself is formed from a combination of cocoa fibers and at least one additional aerosol delivery compound. Alternatively, the wrapping material may merely be used to surround or encompass aerosol delivery agents and compounds, or may, in one embodiment, be both treated with an aerosol delivery compound and surround an aerosol delivery compound.

In forming the wrapping material of the present disclosure, the cocoa shells or husks are first collected and optionally reduced in size. For example, in one embodiment, the cocoa components can be subjected to a grinding operation, milling operation or beating operation that can reduce the size of the cocoa components and/or reduce the cocoa husks into individual fibers. For example, in one embodiment, the cocoa materials including the cocoa shells can be fed to a hammer mill that beats the cocoa materials against a screen for producing a fibrous material.

Figure 2:
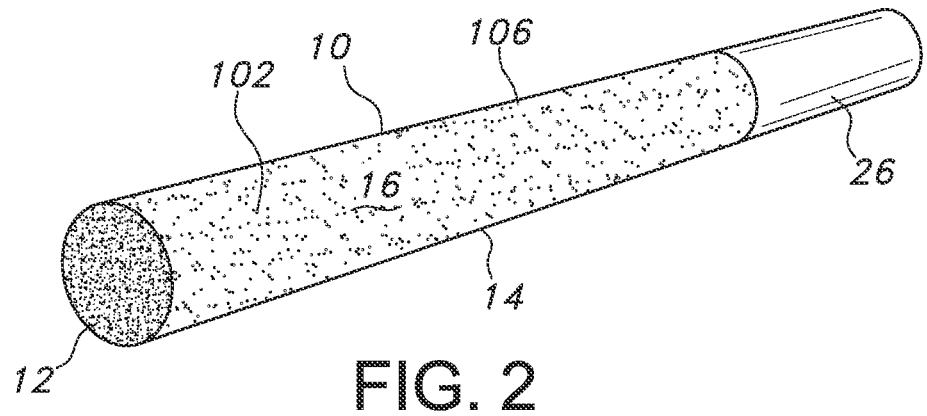
FIG. 2 is a perspective view of one embodiment of a smoking article incorporating the wrapper of the present disclosure.

For instance, referring to FIGS. 1 and 2, it can be seen that, in one embodiment, the web 100 may include pieces or fibers 102 of cocoa husk. Therefore, while the cocoa husks may be ground or refined to be individual fibers, in one embodiment, the cocoa husks may be shredded or refined into pieces.

Nonetheless, the cocoa shells may then be subjected to a gentle extraction process for removing water soluble components. Specifically, the sugars, proteins and colloids (pectins, starches) naturally present in cocoa husks that are extracted in the solvent may give rise to problems, such as bonding to the drying cylinders, difficulties in draining or problems of fermentation in the tanks. In one embodiment, the extraction process may simply include placing the cocoa shells in water and allowing the water soluble portions to be extracted into the water. In an alternative embodiment, various solvents that are water-miscible, such as alcohols (e.g., ethanol), can be combined with water to form an aqueous solvent. The water content of the aqueous solvent can, in some instances, be greater than 50 wt. % of the solvent, and particularly greater than 90 wt. % of the solvent. Deionized water, distilled water or tap water may be employed. The amount of the solvent in the suspension can vary widely, but is generally added in an amount from about 50 wt. % to about 99 wt. %, in some embodiments from about 60 wt. % to about 95 wt. %, and in some embodiments, from about 75 wt. % to about 90 wt. % of the suspension. However, the amount of solvent can vary with the nature of the solvent, the temperature at which the extraction is to be carried out. In one embodiment, the solvent may be heated. Of course, while a variety of solutions may be used, the extraction solution should also be selected so as to be effective for removing soluble compounds while leaving the cocoa fibers unharmed. In one embodiment, for instance, the extraction solution may be a hot aqueous solution that may include water.

The cocoa husks in solvent may optionally be agitated by stirring, shaking or otherwise mixing the mixture in order to increase the rate of solubilization. Typically, the process is carried out for about one-half hour to about 6 hours. Process temperatures may range from about 10° C. to about 100° C., such as from about 40° C. to about 80° C.

After the cocoa materials are soaked and optionally agitated, the insoluble portion of the cocoa husks can be mechanically separated from the soluble portion of the cocoa husks using a press or otherwise separated from the solvent which now contains the soluble portion of the cocoa husks. Once the soluble portion is separated from the insoluble portion, the soluble portion can be discarded or further processed, such as by being concentrated. The soluble fraction can be concentrated using any known type of concentrator, such as a vacuum evaporator. In one embodiment of the present disclosure, the soluble fraction can be highly concentrated. In one embodiment, for instance, the cocoa soluble fraction can be evaporated so as to have a final brix of from about 20% to about 40%, such as from about 25% to about 35%.

While the extraction process removes soluble compounds in order to facilitate the processing of the wrapping material, the extraction process can also be used to remove other undesired compounds. For instance, through the extraction process, pesticides and other compounds may be removed from the soluble portion of the cocoa, and then may be further eliminated from the soluble portion prior to the optional concentration of the soluble portion. While this process is discussed in regards to pesticides, it should be understood that the extraction process may be used to remove undesired compounds from other plants used in the web building fibers, such as tobacco, nicotine, caffeine, and any other compound that is desired to be absent from the final product.

The resulting concentrated cocoa soluble fraction may be discarded, used in a separate process, or can be later coated onto the wrapping material of the present disclosure as will be described in greater detail below.

The resulting insoluble cocoa fraction is generally in an unrefined state. The cocoa material can comprise particles, pieces, and fibers. In one embodiment, the insoluble and extracted cocoa fraction can be subjected to a refining process. For instance, the extracted cocoa husk material can be fed through any suitable refining device, such as a conical refiner or a disks refiner. Other refining devices that may be used include a beater, such as a Valley beater. Refining can occur while the cocoa materials are moist or after being combined with water. For instance, in one embodiment, refining can occur while the cocoa husk material is at a consistency of less than about 10%, such as less than about 5%, such as less than about 3%.

Before or during the refining process, the extracted cocoa husk material is combined with web building fibers and optionally one mineral filler. The web building fibers, such as delignified cellulosic fibers, and the filler can be combined with the cocoa husk material in water or an aqueous solution to form a slurry. Particularly, the present disclosure has unexpectedly found that the combination of the cocoa husk, web building fibers, and at least one filler, allow formation of a web that includes cocoa that has sufficient strength to be formed into a sheet, such as a sheet for a wrapping material. Previously, cocoa webs had been ineffective for forming wrapping materials, as the cocoa webs had lacked the tensile strength and/or other properties needed to form a wrapping material or sheet. Thus, surprisingly, the present disclosure has found that, cocoa husk, web building fibers, and filler may be combined in a slurry, and processed for an amount of time sufficient to form a wrapping material with good strength characteristics, including tensile strength, as well as proper permeability, so as to use the produced web to form a wrapping paper.

The web building fibers can be combined with the extracted cocoa husk material and subjected to a refining process. Alternatively, the extracted cocoa husk material can be fed through a refining process and then combined with the web building fibers. In still another aspect, the extracted cocoa husk material can be fed through a refining process, combined with web building fibers, and then fed through a further refining process.

The amount the extracted cocoa husk material and/or the web building fibers are refined can impact various properties of the resulting web formed later. For instance, increasing the amount the cocoa husk material and/or the web building fibers are refined can make it easier to cut the wrapper. In addition, increasing the amount of refining can also help trap particles and prevent particle loss during handling of the wrapper.

In one aspect, the cocoa husk material and the web building fibers together can have a refining level or refining degree of greater than about 60° SR, such as greater than about 65° SR, such as greater than about 70° SR, such as greater than about 75° SR. The refining level can generally be less than about 100° SR, such as less than about 90° SR, such as less than about 80° SR.

After forming and refining the slurry discussed above, the slurry is then used to form a continuous reconstituted sheet or web. For example, in one embodiment, the slurry is fed to a papermaking process that can include a forming wire, gravity drain, suction drain, a felt press, and a dryer, such as a Yankee dryer, a drum dryer, or the like. For example, in one embodiment, the fiber slurry is formed into a continuous sheet on a Fourdrinier table.

In one embodiment, the fiber slurry is laid onto a porous forming surface and formed into a sheet. Excess water is removed by a gravity drain and/or a suction drain. In addition, various presses can be used to facilitate water removal. The formed sheet can be dried and further treated.

Optionally, the wrapping material that is produced can also be treated with the cocoa soluble portion, such as a concentrated cocoa soluble portion that was separated from the insoluble portion. The cocoa soluble portion can be applied to the web using various application methods, such as spraying, sizing, coating etc. The amount of water soluble cocoa extracts applied to the reconstituted material can depend upon various factors and the anticipated end use application. In general, the water soluble cocoa extracts can be applied to the wrapping material in an amount insufficient to adversely interfere with the neutral taste of the underlying material. For instance, in one embodiment, the water soluble cocoa extracts are applied to the reconstituted material such that the reconstituted material contains water soluble cocoa extracts in an amount up to about 10% by weight, such as in an amount less than about 8% by weight, such as in an amount less than about 6% by weight, such as in an amount less than about 4% by weight, such as in an amount less than about 2% by weight, such as in an amount less than about 1% by weight and generally in an amount greater than about 0.5% by weight. However, in another embodiment of the Invention, the water soluble cocoa extracts can be re-applied in the reconstituted material in an amount greater than about 10% by weight, such as greater than about 15% by weight, such as greater than about 20% by weight, such as greater than about 25% by weight, such as up to about 30% by weight, in order to provide a distinct cocoa aroma to the final smoking article.

While, thus far, the formation of the wrapping material has been described by first extracting and refining the cocoa husk and then mixing the insoluble portion of the cocoa with the refined pulp of web building fibers, it should be understood that one or more types of web building fibers may be mixed with the cocoa husks during the extraction stage, such that the cocoa and the web building fibers undergo extraction, and then a mineral filler is optionally added during the formation of the slurry during the refining process. Of course, as discussed above, the cocoa may be extracted separately, and then mixed with the web building fiber, and optionally a mineral filler during the pulping and refining process.

Notwithstanding the method used to form the web or sheet, in one embodiment, the web building fibers may be fibers of a plant which have undergone extraction in a solvent, for instance, to yield a pulp. While the web building fibers may be obtained from any type of plant, in one embodiment, the web building fibers are delignified cellulosic fibers. For instance, the web building fibers may comprise wood pulp fibers such as softwood fibers or hardwood fibers. Other cellulosic fibers that may be used include flax fibers, hemp fibers, abaca fibers, bamboo fibers, coconut fibers, cotton fibers, kapok fibers, ramie fibers, jute fibers, or mixtures thereof. In one particular embodiment, the reconstituted plant material contains softwood fibers alone or in combination with other fibers such as hardwood fibers, abaca fibers, or the like.

Regardless of the fibers selected to form the web building fibers, the web or wrapping material may include the cocoa materials in an amount of from about 1 to about 99% by weight, such as from about 5% to about 95%, such as from about 20% to about 80%, such as from about 30% to about 70%, such as from about 40% to about 60% cocoa materials by weight, based upon the weight of the web or wrapping material, or any ranges therebetween.

Moreover, the web or wrapping material may include the web building fibers in an amount of from about 1% to about 99% by weight, such as from about 5% to about 95%, such as from about 10% to about 80%, such as from about 20% to about 70%, such as from about 40% to about 60% web building fibers by weight based upon the weight of the wrapping material or web, or any ranges therebetween.

In one aspect, the amount of web building fibers combined with the cocoa materials can be in amounts sufficient to provide integrity to the wrapper. Greater amounts of web building fibers, however, can increase the difficulty in cutting the material. Increased amounts of web building fibers can also lead to a "paper" taste when incorporated into a smoking article. Thus, in one aspect, the web building fibers can be present in the wrapping material or web in an amount generally greater than about 18% by weight, such as in an amount greater than about 20% by weight, such as in an amount greater than about 22% by weight. The web building fibers can also be present in the wrapping material in an amount less than about 30% by weight, such as in an amount less than about 28% by weight, such as in an amount less than about 26% by weight.

In one embodiment, the web building fibers incorporated into the reconstituted plant material include a combination of longer fibers and shorter fibers. The longer fibers can generally have a length of greater than about 2 mm, while the shorter fibers can generally have a length of less than about 1.5 mm. The longer fibers can be used to improve strength and integrity, while the shorter fibers can better retain the cocoa fibers and other components within the fiber substrate. In one embodiment, for instance, the short fibers may be present in the reconstituted plant material in an amount greater than about 5% by weight, such as in an amount greater than about 10% by weight, and generally in an amount less than about 20% by weight. The longer fibers, on the other hand, can be present in the reconstituted web material in an amount greater than about 10% by weight, such as in an amount greater than about 20% by weight, and generally in an amount less than about 50% by weight, such as in an amount less than about 40% by weight. In one embodiment, the shorter fibers comprise hardwood fibers, while the longer fibers comprise softwood fibers. The weight ratio between the longer fibers and the shorter fibers, for example, can be from about 6:1 to about 1:0.75. For instance, the weight ratio between the longer fibers (e.g. softwood fibers) and the shorter fibers (e.g. hardwood fibers) can be from about 4:1 to about 1:1. As described above, the total amount of web building fibers contained in the web can be, in one aspect, from about 18% to about 30%, such as from about 20% to about 28% by weight in conjunction with the above weight ratios.

Regardless of the fibers selected, in one embodiment, the filler can comprise particles incorporated into the reconstituted web material for any desired purpose, such as for facilitating formation of the reconstituted plant material and/or for affecting the appearance or strength of the material. Fillers may include kaolin clay, magnesium oxide, titanium dioxide, calcium carbonate, talc, barium sulfate, a bentonite, a zeolite, a silicate, mica, or a mixture thereof. Furthermore, as the wrapping material according to the present disclosure has a natural color and appearance, it is not necessary to select a white filler. Therefore, additional fillers may be used as are known in the art. The addition of this filler may modify some of the mechanical properties of the wrapping material, in particular the properties allowing it to be printed or written on it. This filler may also give the wrapping material certain sensory properties. The amount of filler in the wrapping material according to the invention is from 0% to 40%, preferably from 5% to 20%, even more preferentially from 10% to 20% by weight of the wrapping material.

Furthermore, in one embodiment, the particle size of the filler may be carefully controlled such that the average particle size of the filler is from about 10 microns or less, such as about 7.5 microns or less, such as from about 5 microns or less, and may also be about 0.1 microns or greater. Of course, in an alternative embodiment, the particle size may be more varied based upon the desired characteristics to be obtained from the filler.

In one embodiment of the invention, the reconstituted cocoa material, without re-applied extracts, might be re-pulped with web building fibers and/or mineral filler, to produce a continuous web with better control of tensile strength and permeability.

Particularly, the present inventors have found that, by forming a wrapping material according to the present disclosure, a web or sheet may be formed using cocoa that has good strength, smoothness, basis weight, and permeability. Thus, a wrapping material according to the present disclosure may be able to withstand a papermaking process, and may also have good sensory characteristics and burn properties. Furthermore, as will be discussed in greater detail below, it was also found that the wrapping material functions well as a carrier for other taste or aerosol delivery agents.

For instance, wrapping materials made in accordance with the present disclosure have excellent mechanical characteristics and have a very desirable and aesthetic appearance. In general, the wrapping material has a basis weight of greater than about 20 gsm, such as greater than about 30 gsm, such as greater than about 40 gsm, such as greater than about 50 gsm, such as greater than about 60, gsm, such as greater than about 70 gsm, such as greater than about 80 gsm, such as greater than about 85 gsm. The basis weight of the wrapping material is generally less than about 100 gsm, such as less than about 90 gsm, such as less than about 80 gsm, such as less than about 70 gsm, such as less than about 60 gsm, such as less than about 50 gsm, or any ranges therebetween. Within the above basis weights, the wrapping material is very strong and can exhibit a tensile strength of greater than about 1,000 cN/15 mm, such as greater than about 1,500 cN/15 mm and generally less than about 4,000 cN/15 mm. Tensile strength can be measured using ASTM Test D828-97.

The wrapping material according to the present disclosure may also have a permeability that facilitates good smoking properties, such as good mainstream smoke control. For instance, the wrapping material according to the present disclosure may have a permeability measured in Coresta units of from about 10 Coresta to about 100 Coresta, such as from about 20 Coresta to about 90 Coresta, such as from about 30 Coresta to about 80 Coresta, such as from about 35 Coresta to about 60 Coresta, or any ranges therebetween.

While the wrapping material according to the present disclosure may naturally or inherently have a desired permeability, in one embodiment, it may be desirable to also perforate the wrapping material after formation. Perforation may be performed as known in the art, and the number and size of the perforations may be selected as needed for the desired application.

In addition to the above physical properties, the wrapping material made in accordance with the present disclosure can exhibit a distinct natural appearance with natural speckling from the one or more cocoa fibers or particles. For instance, again referring to FIGS. 1 and 2, a wrapping material formed according to the present disclosure may have one or more pieces or strands of cocoa husk 102 visible on a surface of the wrapping material 100.

Furthermore, in addition to having a natural appearance, the wrapping material according to the present disclosure may also have a pleasant texture. The wrapping material can have a relatively rough surface, which emphasizes its natural appearance or can be further calendared to provide a smoother feeling.

The wrapping material of the present disclosure also produces smoking articles having better taste properties. For instance, the wrapping material of the present disclosure produces a less papery taste than conventional cigarette papers. Instead, a mild, neutral, and pleasant taste has been observed, even when the wrapping material contains up to about 70% or more web building fibers by weight of the wrapping material. While the wrapping material according to the present disclosure may have more or less web building fibers by weight, it was surprising that the pleasant, neutral taste was maintained even when a large portion of the wrapping material, by weight, was formed of web building fibers.

In addition, the wrapping material produces a cohesive ash with an improved appearance against conventional tobacco wrappers. Particularly, the wrapping material according to the present disclosure exhibits improved ash appearance and combustibility as compared to tradition tobacco wrappers.

While the wrapping material may have a naturally good taste and burn properties, as discussed above, it was also surprisingly found that the wrapping material is a good carrier for other aerosol delivery agents, such as aerosol generating fillers and topical additives which may include flavorants, active ingredients, oils, and extracts. For instance, as discussed above, one example of a topical additive may be the soluble portion of the cocoa husk, which may be optionally concentrated, may be re-applied to the wrapping material after formation of the web to impart further taste and smoke characteristics. Whereas, an aerosol generating filler may be a component from a plant or herb that is incorporated into the reconstituted web for added flavoring or components. Therefore, as used herein, an aerosol delivery agent may be used to refer to both, an aerosol generating filler and/or a topical additive.

Particularly, once the reconstituted plant material has been formed into a fibrous substrate or web as described above, the material can be used as a wrapping material for use in any suitable smoking article. The wrapping material of the present disclosure produces an aerosol or smoke that has a very neutral and pleasing taste. An aerosol generated by the material has no harsh components. In fact, the presence of the extracted cocoa husk can, in some embodiments, produce a roasted cocoa smell and/or taste. Of particular advantage, the wrapping material of the present disclosure is nicotine free and thus can be used to produce a nicotine-free smoking article or a nicotine-free aerosol generating product or can be used to control nicotine delivery in the above products.

In one embodiment, for instance, the wrapping material of the present disclosure can be combined with tobacco during the production of the wrapping material, or may be used to surround a tobacco material to form an aerosol generating material that produces an aerosol or smoke with a controlled amount nicotine in comparison to an aerosol generated by the tobacco material by itself. For example, the wrapping material of the present disclosure can be combined with, or surround, any suitable tobacco material in an amount sufficient to produce an aerosol that contains a controlled amount of nicotine or tobacco flavoring. For instance, in one embodiment, the wrapping material may contain a low amount of nicotine, particularly as compared to a natural tobacco product, and may contain about 0.5% or less nicotine by weight of the wrapping material. Alternatively, a wrapping material may be formed that contains a "high" amount of nicotine as compared to the low nicotine embodiment described above, such that the wrapping material contains greater than about 0.5% nicotine by weight of the wrapping material.

The tobacco material blended with, or surrounded by, the wrapping material of the present disclosure can comprise, for instance, cut leaf tobacco, a reconstituted tobacco material, or mixtures thereof. In one embodiment, the material of the present disclosure can be refined with a tobacco material, in addition to the web building fibers, for forming an aerosol generating material with controlled nicotine deliveries and a desirable taste and smell.

In still another embodiment, the wrapping material of the present disclosure, instead of being combined with, or surrounding, a tobacco material or in addition to being combined with, or surrounding, a tobacco material, may be treated with an aerosol delivery composition containing nicotine. The aerosol delivery composition, for instance, can be topically applied to the wrapping material for incorporating into the material controlled amounts of nicotine. Applying nicotine to the wrapping material can provide numerous benefits and advantages. For example, applying nicotine to the wrapping material allows for precise amounts of nicotine delivery when the wrapping material is converted into an aerosol and inhaled. In addition, the nicotine can be applied to the wrapping material in a manner such that the amount of nicotine contained in an aerosol generated by the material is uniform and consistent from puff to puff. Consequently, in one embodiment, the wrapping material of the present disclosure can be used to produce an aerosol generating material that is neutral and pleasant in taste while still delivering controlled amounts, such as low amounts of nicotine.

For example, in one embodiment, the aerosol delivery composition applied to the wrapping material can contain a low amount of nicotine, particularly as compared to a natural tobacco product, and may contain about 0.5% or less nicotine by weight of the wrapping material. Alternatively, a wrapping material may be formed that contains a "high" amount of nicotine as compared to the low nicotine embodiment described above, such that the wrapping material contains greater than about 0.5% nicotine by weight of the wrapping material. Additionally or alternatively, a tobacco material that may have all or a portion of the nicotine extracted therefrom can be used to produce a tobacco taste and smell while nicotine can be applied separately to the wrapping material in the form of an aerosol delivery composition for better controlling nicotine levels. In this embodiment, the amount of tobacco material in the aerosol generating material can be less than about 50% by weight, such as less than about 40% by weight, such as less than about 30% by weight, such as less than about 20% by weight, such as less than about 10% by weight, and generally greater than about 2% by weight.

In addition to being combined with tobacco materials, it should be understood that the wrapping material of the present disclosure can be combined with any suitable aerosol generating fibers or may surround any suitable aerosol generating filler. For instance, the reconstituted plant material of the present disclosure can also be combined with aerosol generating fillers made from other plant materials, such as herbal plants, botanical plants, and trees, including herbs, plants and trees that may be used to form smokable fibers or herbal smokeable articles, such as cocoa tree, coffee tree or coffee bean, tea tree or tea leaf, vine, ginger, ginkgo, camomile, tomato, ivy, maté, rooibos, cucumber, mint, a cereal such as wheat, barley or rye, or other trees such as broadleaved or resinous trees, and the like, as well as combinations thereof.

In addition to nicotine, the wrapping material of the present disclosure is well suited to receiving other aerosol delivery agents. The wrapping material, for instance, is highly absorbable and can contain up to 40% by weight of topical additives. In this regard, the wrapping material of the present disclosure is also well suited to acting as a carrier for various different aerosol delivery compositions. Each aerosol delivery composition, for instance, can contain one or more aerosol delivery agents.

Aerosol delivery compositions that can applied to the wrapping material of the present disclosure include solutions, suspensions, oils, and the like. Solutions and suspensions, for instance, can be applied to the wrapping material and later dried leaving behind a solid residue within the fiber substrate.

In one embodiment, an aerosol delivery composition may be obtained by extracting a plant substance from a plant for application to the wrapping material. Additionally or alternatively, the present disclosure may include a step for isolating at least one compound from a plant substance, concentrating a plant substance, or even a purifying or eliminating a compound from a plant substance, in order to obtain a modified plant substance to be applied to the wrapping material. While optional, such a process may result in the transformation of an original raw plant substance into a modified plant substance, whether in the form of dry extracts, liquid extract, a liquor or an isolated substance, based upon the desired end properties of the plant substance to be applied to the wrapping material. Of course, while the plant substance may be an original plant substance or a modified plant substance, in one embodiment, the plant substance is applied to the wrapping material without undergoing any further processing after extraction. Furthermore, while the aerosol delivery composition has been described as being extracted from a plant, it should be understood that synthetic or naturally occurring aerosol delivery compositions (e.g. without needing to be extracted) may also be used.

Examples of aerosol delivery agents that may be contained in the aerosol delivery composition include, or may be an extract of, (in addition to nicotine) sugars, licorice extracts, menthol, honey, coffee extracts, maple syrup, tobacco extracts, botanical extracts, plant extracts, tea extracts, fruit extracts, flavorings such as clove, anise, cinnamon, sandalwood, geranium, rose oil, vanilla, caramel, cocoa, lemon oil, cassia, spearmint, fennel, or ginger, fragrances or aromas such as cocoa, vanilla, and caramel, medicinal plants, vegetables, spices, roots, berries, bar, seeks, essential oils and extracts thereof, such as anise oil, clove oil, carvone and the like, artificial flavoring and fragrance materials such as vanillin, and mixtures thereof. The extracts applied to the wrapping material can be water soluble or oil soluble. Thus, various different carrier liquids can be used to apply the aerosol delivery agents to the wrapping material.

In one embodiment, the wrapping material of the present disclosure can be used as a carrier for components obtained from *cannabis*. *Cannabis*, for instance, has recently been legalized in many states in the United States for both medical and recreational use. In addition, various chemicals and compounds contained in *cannabis* are becoming more and more popular drugs for pain relief in lieu of conventional pain relief medicines, such as opioids. *Cannabis*, for instance, contains various cannabinoids that can be used for pain relief. Inhaling an aerosol created by *cannabis* is the most common and least expensive method for delivering drugs contained in *cannabis* to a user. Unfortunately, however, merely inhaling aerosol generated from dried *cannabis* buds or leaves can lead to non-uniform deliveries of the pain relief drugs contained in the plant. Deliveries of the cannabinoids, for instance, can vary dramatically depending upon the particular plant and the particular plant parts being used to generate the aerosol. In addition, cannabinoid deliveries can vary dramatically based upon other factors such as the packing density of the material, the particular type of aerosol-generating device or smoking article used to produce an aerosol, and the like. In addition, aerosols created from *cannabis* plant can contain irritants and produce a relatively harsh aerosol or smoke.

Cannabinoids that can be incorporated into the wrapping material of the present disclosure include cannabidiol (CBD) and tetrahydrocannabinol (THC). THC contained in *cannabis* acts on specific receptors in the brain which lead to a feeling of euphoria and a relaxed state. CBD, on the other hand, also interacts with pain receptors in the brain but does not create the same euphoric feeling caused by THC. In accordance with the present disclosure, in one embodiment, THC can be applied to the wrapping material of the present disclosure, CBD can be applied to the wrapping material or, alternatively, both THC and CBD can be applied to the wrapping material.

In addition to THC and CBD, various other cannabinoids can also be incorporated into an aerosol delivery composition and applied to the wrapping material in accordance with the present disclosure. For instance, other cannabinoids contained in *cannabis* include cannabichromene, cannabinol, cannabigerol, tetrahydrocannabivarin, cannabidivarin, cannabidiolic acid, other cannabidiol derivatives, and other tetrahydrocannabinol derivatives. The above cannabinoids can be used singularly or in any combination and applied to the wrapping material.

The cannabinoids described above can be applied to the wrapping material using various different methods. For instance, in one embodiment, the cannabinoid, such as CBD, can be formulated into a water soluble form or powder that can be applied to the wrapping material as a solution or aqueous suspension. Alternatively, a *cannabis* oil extract may be obtained from raw *cannabis* plants. The oil extract may contain THC alone, CBD alone, or a combination of THC and CBD. The oil extract can be applied to the wrapping material so that an aerosol generated by the material contains controlled amounts of the cannabinoids. In addition to containing controlled amounts of the cannabinoids, the wrapping material can also be designed to provide uniform deliveries of the cannabinoids in the aerosol generated from the material.

Another component that can be added to the wrapping material are various flavorants, especially terpenes. A terpene or a blend of terpenes, for instance, can be used to develop desirable aromas and indicate to the user the quality of the product. One or more terpenes can also improve the sensory reaction to inhaling an aerosol created by the wrapping material.

Various different terpenes can be applied to the wrapping material. Such terpenes include but are not limited to pinene, humulene, b-caryophyllene, isopulegol, guaiol, nerylacetate, neomenthylacetate, limonene, menthone, dihydrojasmone, terpinolene, menthol, phellandrene, terpinene, geranylacetate, ocimene, myrcene, 1,4-cineole, 3-carene, linalool, menthofuran, perillyalcohol, pinane, neomenthylaceta, alpha-bisabolol, borneol, camphene, camphor, caryophyllene oxide, alpha-cedrene, beta-eudesmol, fenchol, geraniol, isoborneol, nerol, sabinene, alpha-terpineol, and mixtures thereof.

In one embodiment, various different terpenes can be blended together in order to mimic the ratios of terpenes found in natural *cannabis* plants. For instance, from about 2 to about 12 terpenes can be blended together and applied to the wrapping material. Each terpene can be applied to the wrapping material in an amount greater than about 0.001% by weight and generally less than about 2% by weight. For instance, each terpene can be applied in an amount from about 0.01% by weight to about 1.5% by weight. For instance, each terpene can be applied in an amount from about 0.1% to about 1.1% by weight.

Exemplary blends of terpenes include alpha-pinene, beta-caryophyllene, and beta-pinene; alpha-humulene, alpha-pinene, beta-caryophyllene, beta-pinene, and guaiol; beta-caryophyllene, beta-pinene, and d-limonene; beta-caryophyllene, beta-pinene, and nerolidol; beta-caryophyllene, beta-pinene, d-limonene, and terpinolene; alpha-bisabolol, alpha-pinene, beta-caryophyllene, beta-myrcene, beta-pinena, and d-limonene; beta-caryophyllene, beta-pinena, and p-cymene; alpha-humulene, beta-caryophyllene, beta-pinene, d-limonene, linalool, and nerolidol; beta-caryophyllene and beta-pinene; beta-caryophyllene, beta-myrcene, and terpinolene; alpha-pinene, beta-caryophyllene, beta-pinene, d-limonene; alpha-humulene, alpha-pinene, beta-caryophyllene, beta-myrcene, beta-pinena, d-limonene, and guaiol.

Figure 3:
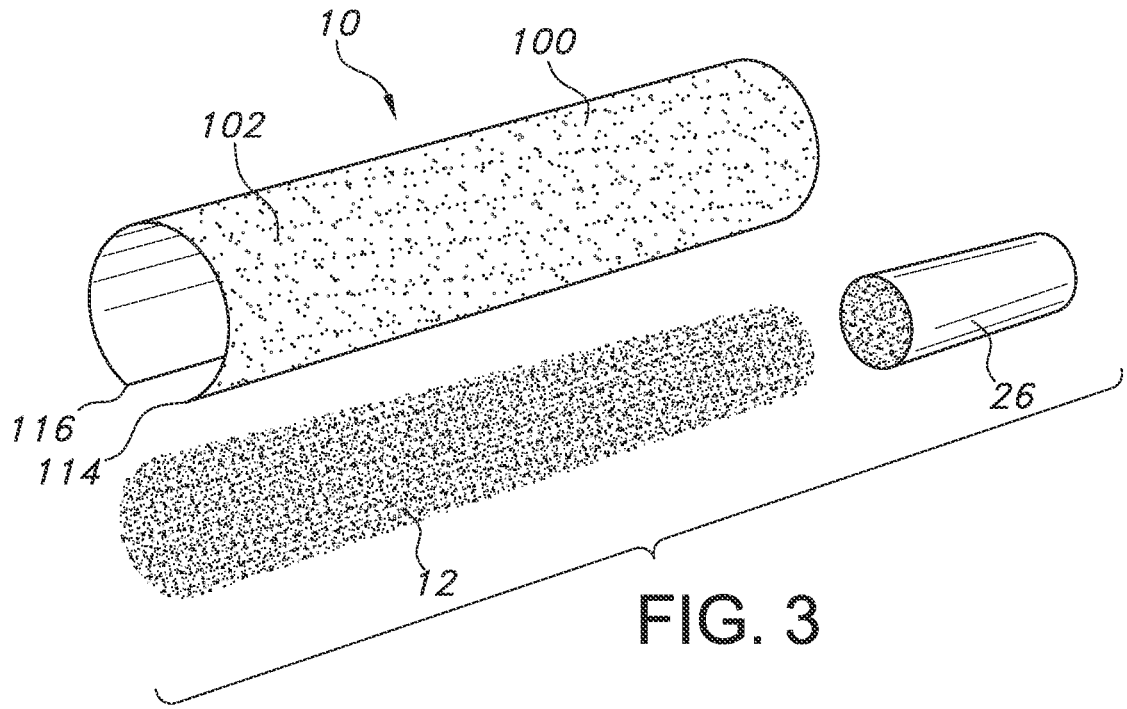
FIG. 3 is an exploded view of the smoking article illustrated in FIG. 1.

Regardless of the aerosol delivery composition and agent selected, the wrapping material according to the present disclosure may be used as a carrier for the aerosol delivery composition and agent. As the wrapping material has a pleasant neutral taste and smell, the wrapping material may then exhibit a taste and smell imparted by the aerosol delivery composition and agent. The aerosol delivery composition and agent may be contained in the wrapping material in an amount greater than about 0.1% by weight, such as at least about 1% or greater, such as at least about 5% or greater, such as at least about 10% or greater, such as at least about 15% or greater, such as at least about 20% or greater, such as at least about 25% or greater, such as at least about 30% or greater, such as at least about 35% or greater, such as 40% or less. Of course, in one embodiment, the soluble portion of the cocoa extract may be reapplied to the wrapping material. While the soluble portion may be applied in any amount as discussed above in regards to the aerosol delivery agent, the soluble portion of the cocoa husk may be contained in the wrapping material in an amount greater than about 0.1% by weight, such as at least about 1% or greater, such as at least about 5% or greater, such as at least about 10% or greater, such as at least about 15% or greater, such as at least about 20% or greater, such as at least about 25% or greater, such as at least about 30% or greater, such as at least about 35% or greater, such as 40% or less. Wrapping materials made according to the present disclosure can be incorporated into all different types of smoking articles and aerosol-generating materials. For illustrative purposes only, one such smoking article is shown in FIGS. 2 and 3. As shown, the smoking article 10 includes a smokable column 12. The smoking article 10 may also include a wrapping material 100 that defines an outer circumferential surface 16 when wrapped around the smokable column 12. The article 10 may also include a filter 26 that may be enclosed by a tipping paper.

The smoking article shown in FIGS. 2 and 3 generally comprises a cigarette. In other embodiments, however, the wrapping material of the present disclosure can be used to produce cigarillos and little cigars. While not shown, a cigarillo, for example, can include a plastic tip.

Figure 4A:
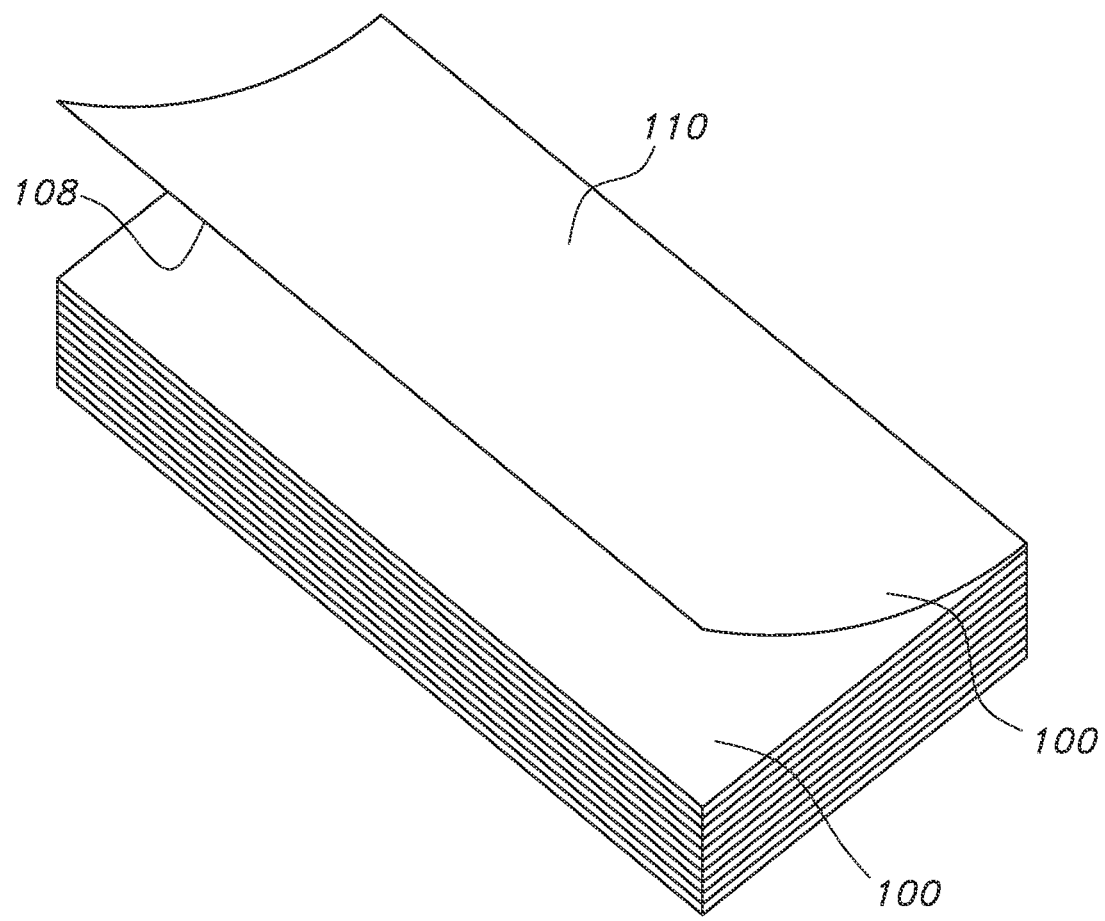
FIG. 4A is a perspective view of a stack of roll-your-own wrappers made in accordance with the present disclosure.
Figure 4B:
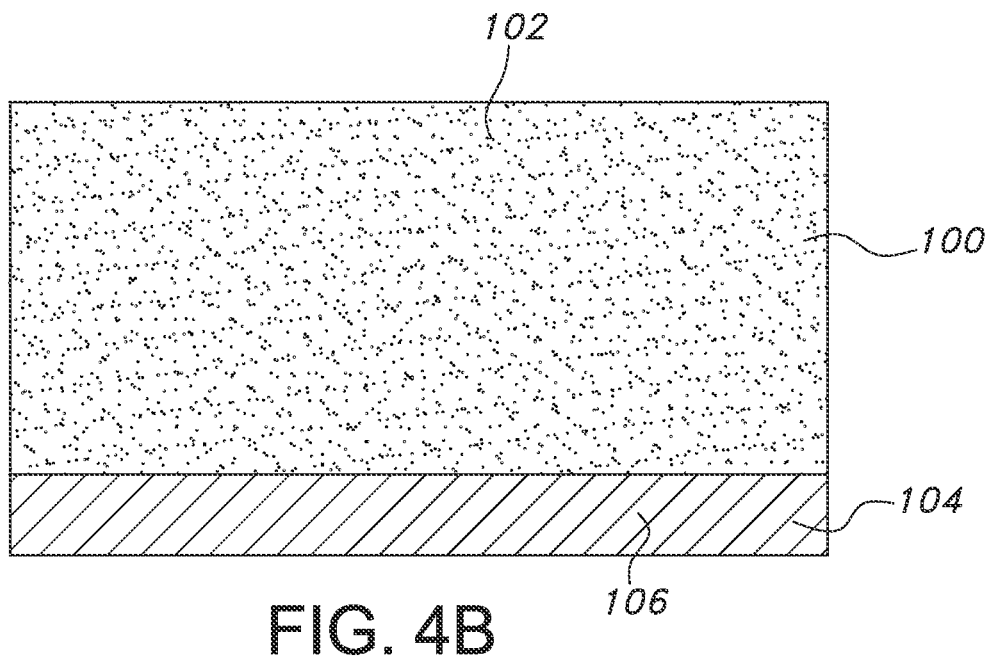
FIG. 4B is a plan view of one of the wrappers contained in the stack in FIG. 4A.

Notwithstanding the articles that may utilize a wrapping material 100 according to the present disclosure, FIG. 4a shows an embodiment of the present disclosure wherein the wrapping material 100 is formulated as a booklet of individual wrapping materials 100 affixed to one or more adjacent wrapping materials 100 via a natural, or at least smokable or edible, adhesive 104. As shown in FIG. 4b, in one embodiment, the adhesive 104 may only be located on a portion of the wrapping material 100, such as on an edge 106 thereof. Additionally or alternatively, the adhesive may only be located on a first side 108, which is opposite a second side 110. In such an embodiment, the first side 108 of a first wrapping material 100 may have an adhesive 104 located thereon, and may be oriented so as to be placed in contact with a second side 110 of an adjacent piece of wrapping material 100. As such, each piece of wrapping material 100 may have adhesive on a single side, so as to adhere to an immediately adjacent piece of wrapping material 100 or to a backing material 112. However, it should be understood that, in an alternative embodiment, the adhesive 104 may be located on both sides, 108 and 110, or on one or more portions of either side 108 and 110.

Regardless of the manner in which the adhesive is applied, the adhesive may be selected to be "resealable" in that the adhesive may serve to releasably affix a piece of wrapping material 100 to an adjacent piece of wrapping material 100, until such a time as a user wishes to remove a piece of wrapping material 100 from an adjacent piece of wrapping material. At such a point, the adhesive 104 may retain its adherence properties, and may serve to adhere to a portion of the wrapping material 100 to which the adhesive 104 has been applied, such as, for example, referring to FIG. 3, the adhesive 104 may adhere a first edge 114, or an area of the wrapping material adjacent to the first edge 114, of the wrapping material 100 to a second edge 116, or area of the wrapping material adjacent to the second edge 116, when forming a smoking article. Of course, the adhesive 104 may also be used to attach the wrapping material 100 to a second piece of wrapping material 100, or to any portion on either side of the wrapping material 100 to which the adhesive 104 has been applied. For instance, an embodiment where an adhesive 104 may be utilized or desired, is for hand-rolled smoking articles.

Regardless, while a seal or resealable material, such as an adhesive, may be applied by many different processes, in one embodiment, the sealable material or adhesive is applied by an off-line process or on-line sizing process. Either method, or another method, may be used to apply an adhesive 104 to at least one portion, such as at least two portions, at least three portions, or more portions of the wrapping material, and in one embodiment, may be used to apply an adhesive 104 to all or a majority of at least one side of the wrapping material. Nonetheless, when off-line gumming is used to apply the adhesive 104, the adhesive 104 may be applied by various techniques including coating, spraying, and printing. Conversely, on-line sizing may include adding one or more adhesives 104 to a size-press during the production of the wrapping material.

Notwithstanding the manner in which the adhesive 104 is applied to the wrapping material 100, in one embodiment, the adhesive may include alginates, arabic gum, guar gum, pectin, polyvinyl alcohol, polyvinyl acetate, cellulose derivatives such as ethyl cellulose, methyl cellulose, and carboxymethyl cellulose, starch, starch derivatives, and the like.

In one particular embodiment, the adhesive material may include an arabic gum, cellulose, and/or cellulose derivatives. In one embodiment, cellulose derivatives include carboxy methyl cellulose (CMC), methylcellulose (MC), and hydroxypropyl methyl cellulose (HPMC). Of course, it should be understood that other adhesive materials may be used as known in the art.

Regardless of the adhesive used, the adhesive may be present on the wrapping material or web in an amount of from about 0.1% to about 15% by weight, such as from about 2% to about 5% by weight.

In one embodiment, smoking articles made according to the present disclosure can also have reduced ignition propensity characteristics. For instance, the wrapping material of the present disclosure may be used as an outer wrapper of the smoking article, and can include a plurality of discrete reduced ignition areas spaced in the axial direction of the smoking article. For instance, in one embodiment, the discrete reduced ignition areas may be in the form of circular bands. The bands can have a width so that oxygen is limited to the burning coal for a sufficient length or period of time to extinguish the coal if the smoking article were left in a static burn condition. The bands, for instance, can have a width of generally greater than about 3 mm, such as greater than about 4 mm, such as greater than about 5 mm, and generally less than about 10 mm, such as less than about 8 mm, such as less than about 7 mm.

The spacing between the reduced ignition areas can also vary depending upon a number of variables. The spacing should not be so great that the cigarette burns for a sufficient length of time to ignite a substrate before the coal burns into a reduced ignition area. The spacing also affects the thermal inertia of the burning coal, or the ability of the coal to burn through the reduced ignition areas without self-extinguishing. In general, the band spacing should be greater than about 5 mm, such as greater than about 10 mm, such as greater than about 15 mm, and generally less than about 50 mm, such as less than about 40 mm, such as less than about 30 mm. Each smoking article can contain from about 1 to about 3 bands.

In general, any suitable ignition reducing composition can be applied to the outer wrapper/wrapping material of the smoking article. In one embodiment, for instance, the ignition reducing composition contains a film-forming material. For example, film-forming materials that can be used in accordance with the present invention include alginates, guar gum, pectin, polyvinyl alcohol, polyvinyl acetate, cellulose derivatives such as ethyl cellulose, methyl cellulose, and carboxymethyl cellulose, starch, starch derivatives, and the like.

In one particular embodiment, the film-forming material may comprise an alginate, alone or in combination with starch. In general, an alginate is a derivative of an acidic polysaccharide or gum which occurs as the insoluble mixed calcium, sodium, potassium and magnesium salt in the Phaeophyceae brown seaweeds. Generally speaking, these derivatives are calcium, sodium, potassium, and/or magnesium salts of high molecular weight polysaccharides composed of varying proportions of D-mannuronic acid and L-guluronic acid. Exemplary salts or derivatives of alginic acid include ammonium alginate, potassium alginate, sodium alginate, propylene glycol alginate, and/or mixtures thereof.

In one embodiment, a relatively low molecular weight alginate may be used. For example, the alginates may have a viscosity of less than about 500 cP when contained in a 3% by weight aqueous solution at 25° C. More particularly, the alginates may have a viscosity of less than 250 cP at the above conditions, particularly less than 100 cP, and in one embodiment at a viscosity of about 20-60 cP. As used herein, viscosity is determined by a Brookfield LVF Viscometer with a suitable spindle according to the viscosity. At the above lower viscosity levels, alginate compositions can be formed at a higher solids content, but yet at a low enough solution viscosity to permit the application of the composition to a paper wrapper using conventional techniques. For example, the solids content of an alginate solution made in accordance with the present invention can be greater than about 6%, particularly greater than about 10%, and more particularly from about 10% to about 20% by weight.

At the above solids levels, alginate compositions used in accordance with the present invention can have a solution viscosity of greater than about 250 cP, particularly greater than about 500 cP, more particularly greater than about 800 cP, and in one embodiment at a viscosity of greater than about 1,000 cP at 25° C. In general, the solution viscosity of the alginate film-forming composition can be adjusted depending upon the manner in which the composition is being applied to the wrapper. For instance, the solution viscosity of the composition can be adjusted depending upon whether or not the composition is being sprayed onto the paper or printed onto the paper.

In other embodiments, it should also be understood that depending upon the application a relatively high molecular weight alginate may be used. For example, the alginate may have a viscosity of greater than about 500 cP when contained in a 3% by weight aqueous solution at 25° C.

In addition to the film-forming material, the reduced ignition composition applied to the wrapper can contain various other ingredients.

For instance, in one embodiment, a filler can be contained within the composition. The filler can be, for instance, calcium carbonate, calcium chloride, calcium lactate, calcium gluconate, and the like. In addition to calcium compounds, other various particles may be used including magnesium compounds such as magnesium oxide, clay particles, and the like.

The ignition reducing composition, in one embodiment, can be water based. In particular, the ignition reducing composition may comprise an aqueous dispersion or aqueous solution. Alternatively, the ignition reducing composition prior to being applied to the paper wrapper may comprise a non-aqueous solution or dispersion. In this embodiment, for instance, an alcohol may be present for applying the composition to the wrapper.

As opposed to a film-forming composition, the ignition reducing composition may also comprise a cellulose slurry (a type of dispersion). As used herein, a slurry containing papermaking materials is not a film-forming composition. The cellulose slurry applied to the paper substrate may comprise fibrous cellulose, one or more fillers, and/or cellulose particles. As used herein, cellulose fibers and cellulose particles are to be differentiated from derivatized cellulose such as carboxymethyl cellulose. Cellulose fibers and cellulose particles, for instance, are not water soluble. In one embodiment, the cellulose slurry applied to the paper substrate may comprise microcrystalline cellulose.

Once the ignition reducing composition is formulated, the composition can be applied to a paper wrapper in discrete areas. The manner in which the composition is applied to the paper wrapper can vary. For example, the composition can be sprayed, brushed, applied with a moving orifice, or printed onto the wrapper. To form a treated area, the composition can be applied in a single pass or in a multiple pass operation. For instance, the composition can be applied to the wrapping paper in successive steps in order to form areas on the paper having reduced ignition proclivity. In general, during a multiple pass process, the treated areas can be formed by applying the composition during from about 2 to about 8 passes.

The amount of reduced ignition composition applied to the wrapper can also vary. For instance, the composition can be applied to the wrapper in an amount less than about 15% by weight, such as less than about 10% by weight, such as less than about 8% by weight. In general, the composition is applied in an amount greater than 1% by weight based upon the weight of the composition within the reduced ignition areas.

As used herein, the above weight percentages are based on the area treated with the chemical components. In other words, the weight percentages above for the reduced ignition composition is the amount applied within the treated areas as opposed to the total amount applied over the entire surface of the wrapper.

Through the process of the present disclosure, reduced ignition areas can be produced having a relatively high permeability while also having a relatively low diffusivity. For instance, the reduced ignition areas can have a permeability greater than 10 CORESTA while still being capable of producing smoking articles that pass ASTM Test E2187-09 at least 75% of the time.

In general, the reduced ignition areas have a diffusivity that is relatively low. The diffusivity can be measured at room temperature (23° C.). In general, the diffusivity at 23° C. of the reduced ignition areas is less than about 0.5 cm/s, such as less than 0.4 cm/s, such as less than 0.3 cm/s. In one embodiment, the reduced ignition areas may have a diffusivity of greater than about 0.05 cm/s, such as greater than about 0.15 cm/s, such as greater than 0.16 cm/s, such as greater than 0.17 cm/s, while still having the desired reduced ignition proclivity characteristics. Diffusivity is measured using a Sodim $CO_2$ diffusivity tester.

While additives may not be necessary in the wrapping material, as the wrapping material according to the present disclosure naturally has good manufacturing properties (e.g. tensile strength) and sensory properties, generally, a wrapping material according to the present disclosure may include one or more additives. Additives may be used for manufacturing wrapping papers so as to develop or give the wrapping material new properties, for instance chemical, optical, sensory or mechanical properties such as tear strength or folding resistance. In one embodiment, an additive may be a humectant, burn control additives, gums, wet strength agent, an oil-barrier and fat-barrier agent, a antiblocking agent, a dry strength agent, a softener, a wetting agent or lattices.

In one embodiment, the reconstituted web material can further contain a humectant. The humectant can be incorporated into the wrapping material for various different reasons in order to provide different benefits and advantages. For instance, in one embodiment, a humectant may be incorporated into the wrapping material in order to improve the processability and handling of the resulting fiber substrate.

While various humectants may be incorporated into the wrapping material of the present disclosure, humectants may include a polyol, a non-polyol or a mixture thereof. Typically a polyol generating agent may be sorbitol, glycerol, propylene glycol, triethylene glycol or a mixture thereof. Typically a non-polyol generating agent may be lactic acid, glyceryl diacetate, glyceryl triacetate, triethyl citrate or isopropyl myristate or a mixture thereof. In one embodiment, the humectant is glycerol, propylene glycol, or a mixture of glycerol and propylene glycol, glycerol being preferred glycerol, propylene glycol, or mixtures thereof. Regardless of the humectant selected, the humectant may be present in the wrapping material in an amount of from 0.1% to about 5% by weight of the wrapping material, such as from about 0.5% to about 4.5%, such as from about 1% to about 4% by weight of the wrapping material, or any ranges therebetween.

The burn control agent, for instance, may comprise a salt of a carboxylic acid. For example, the burn control agent may comprise an alkali metal salt of a carboxylic acid, an alkaline earth metal salt of a carboxylic acid, or mixtures thereof. Examples of burn control agents that may be used include a salt of acetic acid, citric acid, malic acid, lactic acid, tartaric acid, carbonic acid, formic acid, propionic acid, glycolic acid, fumaric acid, oxalic acid, malonic acid, succinic acid, nitric acid, phosphoric acid, or mixtures thereof. Particular burn controlling agents that may be used include potassium citrate, sodium citrate, potassium succinate, sodium succinate, or mixtures thereof. When present, the burn control agent can be applied to the wrapping material generally in an amount greater than about 0.1% by weight, such as in an amount greater than about 0.5% by weight, such as in an amount greater than about 1% by weight and generally less than about 5% by weight, such as less than about 4% by weight, such as less than about 3% by weight, such as less than about 2% by weight.

Gums may include alginates, guar gum, pectin, polyvinyl alcohol, polyvinyl acetate, cellulose derivatives such as ethyl cellulose, methyl cellulose, and carboxymethyl cellulose, starch, starch derivatives, and the like. In one particular embodiment, the gum may comprise an alginate, alone or in combination with starch. In general, an alginate is a derivative of an acidic polysaccharide or gum which occurs as the insoluble mixed calcium, sodium, potassium and magnesium salt in the Phaeophyceae brown seaweeds. Generally speaking, these derivatives are calcium, sodium, potassium, and/or magnesium salts of high molecular weight polysaccharides composed of varying proportions of D-mannuronic acid and L-guluronic acid. Exemplary salts or derivatives of alginic acid include ammonium alginate, potassium alginate, sodium alginate, propylene glycol alginate, and/or mixtures thereof. Gums may be used in addition to adhesive agents, or in one embodiment, the gum serves as the adhesive agent, and is provided as part of the web instead of being applied to an exterior of the wrapping material as discussed above.

A wet strength agent may reduce the potential for degradation of the wrapping material if the latter is placed in contact with a liquid, such as water. Typically, the wet strength agent may be chosen from polyamides, such as epichlorohydrin resin, a polyamine-epichlorohydrin resin, a poly(aminoamide)-epichlorohydrin resin, a urea-formaldehyde resin, a melamine-formaldehyde resin; an alkyl-ketene dimer; alkylsuccinic anhydride; a polyvinylamine; an oxidized polysaccharide. Typically, the amount of wet strength agent is from 0.1% to 30%, preferably from 1% to 15%, even more preferentially from 5% to 10% by dry weight of the wrapping material.

A antiblocking agent may limit the adhesion of a material to the paper. Typically, the antiblocking agent may be chosen from carboxymethylcellulose, polyacrylamides, acrylic esters, silicones and latices.

A dry strength agent may increase the resistance of the wrapping material if the latter is subjected to large mechanical stresses. The dry strength agent may be chosen from starches and modified gums, cellulose polymers, synthetic polymers, for instance carboxymethylcellulose and polyacrylamides. Typically, the amount of dry strength agent is from 0.1% to 15%, preferably from 1% to 10%, even more preferentially from 1% to 5% by dry weight of the wrapping material.

A softener may improve the softness of the wrapping material. Typically, a softener is a fatty acid, a siloxane compound, a silicone compound, an aminosilicone compound, an extract of aloe vera, an extract of sweet almond, an extract of camomile, a quaternary ammonium compound. Typically, the amount of softener is from 0.1% to 30%, preferably from 1% to 15%, even more preferentially from 5% to 10% by dry weight of the wrapping material.

The finished web or wrapper is dried and wound into rolls. For instance, in one embodiment, the dried sheet is wound into bobbins having a width of from about 15 mm to about 54 mm, such as from about 19 mm to about 28 mm. Prior to winding the web into a bobbin, the web may be calendered to increase the smoothness and runnability of the material. In one embodiment, for instance, a multi-nip calendar device may be used.

Wrapping materials made in accordance with the present disclosure have excellent mechanical characteristics and have a very desirable and aesthetic appearance. The aesthetic appearance can be further improved by the addition of dyes (synthetic and/or natural) and filigreeing technologies.

The present disclosure may be better understood with reference to the following examples.

EXAMPLES

The following test methods are used to not only define the various parameters but also were used in obtaining the results in the examples below.

Tests & Methods

In the following examples, dry basis weight was obtained by taking a 10 $cm^2$ sample of the final wrapping material product The sample is dried in a speed dryer for 10 at a temperature of 93° C.

The final weight is measured with a 0.1 g accuracy to determine the dry basis weight per $m^2$;

Results are reported in the units grams per meter squared ($g/m^2$ or gsm).

Porosity is determined using ISO 2965 and is reported in the units of the Coresta air permeability unit (CU).

Tensile strength in the machine direction was determined using ISO test 1924-2, except that the samples were not conditioned prior to testing, and all results are reported in the units of cNewtons per 15 millimeters (cN/15 mm).

Example 1

A cocoa wrapper according to the invention was manufactured according to the following method:

Reconstituted cocoa fibers made of approximately 60% *Cocoa* husks were prepared according to the following method: cocoa husks were ground using a hammer mill so as to obtain particles about 10 mm in size. The ground husk material was then mixed with softwood fibers and the mixture was pulped in water at 70° C. for 30 minutes, at a husk fiber and softwood fiber to water ratio of 1/10. The mixture was then pressed so as to separate the soluble portion (soluble cocoa husk portion) from the insoluble portion (insoluble cocoa husk fibers). The insoluble portion was then refined using disc refiners. After refining, the slurry containing the reconstituted cocoa fibers and softwood fibers is processed on a paper-machine, threshed in strips, and packed at a mixture of approximately 10% reconstituted cocoa fiber based upon the dried weight of the final product, to yield a web or sheet having a dry basis weight of 70 gsm. The sheet or web formed of the reconstituted cocoa fibers was further re-pulped in a pulping tank with bleached softwood pulp at a ratio of reconstituted cocoa husk fibers to softwood pulp of 1:4 and temperature of approximately 40° C. Calcium carbonate, used as a filler, was then added to the mixed pulp at a ratio of filler to mixed pulp of 1:4. The mixed pulp is then refined on double-disk refiners, screened through fiber screens and then formed onto a continuous sheet, using a paper making process with a Fourdrinier table and can dryers. The resulting cocoa sheet is sized through a double-roller coating press with a glycerol humectant and a potassium citrate burn control agent in an amount such that each of the humectant and the potassium citrate are present on the dried wrapping material in an amount of 1.2% by weight, based upon the dry weight of the wrapping material, respectively.

The final wrapping material product contained cocoa husks fibers in an amount of about 10% by weight of the dried web, a dry basis weight of 43 gsm, a porosity of 25 CU, and Tensile strength of 1,850 cN/15 mm.

Example 2

The same method as used in Example 1 was repeated, except that lower refining pressure was applied after re-pulping the reconstituted cocoa fibers in order to increase the porosity. Additionally, the amount of potassium citrate burn control agent was increased so as to be present on the dried wrapping material in an amount of 2.4% by weight, based upon the dry weight of the wrapping material, to improve the burning properties.

The final wrapping material product contained cocoa husks fibers in an amount of 10% by weight of the dried web, a dry basis weight of 43 gsm, a porosity of 45 CU, and Tensile strength of 1,680 cN/15 mm.

Example 3

A cocoa wrapper according to the invention was manufactured according to the same method as described in Example 1 except that the reconstituted cocoa fibers were re-pulped in a pulping tank with bleached softwood pulp at a ratio of reconstituted cocoa fibers to softwood pulp at a ratio of 1:1 and temperature of approximately 40° C.; a calcium carbonate filler was added to the mixed pulp at a ratio of filler to mixed pulp of 1:4. The resulting web of reconstituted cocoa is sized through a double-roller coating press with a glycerol humectant and a potassium citrate burn control agent such that each of the humectant and the potassium citrate are present on the dried wrapping material in an amount of 1.2% by weight, based upon the dry weight of the wrapping material, respectively.

The final wrapping material product contained cocoa husks fibers in an amount of about 30% by weight of the dried web, a dry basis weight of 43 gsm, a porosity of 36 CU, and Tensile strength of 1,850 cN/15 mm.

Example 4

Example 3 was repeated but the amount of potassium citrate burn control agent was increased so as to be present on the wrapping material in an amount of 2.4% by weight, based upon the dry weight of the wrapping material, to improve the burning properties.

The final wrapping material product contained cocoa husks fibers in an amount of 30% by weight of the dried web, a dry basis weight of 43 gsm, a porosity of 38 CU, and Tensile strength of 1,710 cN/15 mm.

Various different embodiments of wrapping materials can be made in accordance with the present disclosure. In addition, the embodiments can be combined together to form new embodiments. In one embodiment, a wrapping material is provided that comprises a web. The web comprises extracted cocoa husk fibers combined with web building fibers. The web building fibers comprise delignified cellulosic fibers. The web can have a basis weight of from about 20 gsm to about 80 gsm and can have a permeability of from about 10 Coresta to about 100 Coresta.

The web building fibers combined with the extracted cocoa husk fibers in any of the embodiments described above can vary. In an embodiment, the web building fibers are pulp fibers, such as softwood fibers, hardwood fibers, or mixtures thereof. In an embodiment, the web building fibers contain softwood fibers and hardwood fibers in a ratio of from 1:2 to 2:1. In an embodiment, the web building fibers comprise flax fibers. In an embodiment, the web building fibers are abaca fibers. In an embodiment, the web building fibers are bamboo fibers. In an embodiment, the web building fibers are coconut fibers. In an embodiment, the web building fibers are ramie fibers. In an embodiment, the web building fibers are jute fibers. In an embodiment, the web building fibers are hemp pulp fibers. The hemp pulp fibers can be used alone or in combination with wood pulp fibers, such as softwood fibers, hardwood fibers, or mixtures thereof. In an embodiment, the web building fibers are present in the wrapping material in an amount greater than about 3% by weight. In an embodiment, the web building fibers are present in the wrapping material in an amount greater than 5% by weight. In an embodiment, the web building fibers are present in the wrapping material in an amount greater than about 8% by weight. In an embodiment, the web building fibers are present in the wrapping material in an amount greater than about 12% by weight. In an embodiment, the web building fibers are present in the wrapping material in an amount greater than about 18% by weight. In an embodiment, the web building fibers are present in the wrapping material in an amount less than about 50% by weight, such as in an amount less than about 40% by weight.

In an embodiment, the extracted cocoa husk fibers can be combined with the web building fibers in a manner that produces a uniform speckled appearance over a surface of the wrapping material. In an alternative embodiment, the wrapping material may display a solid, single color.

In an embodiment, the wrapping material may include a web comprising extracted cocoa husk fibers combined with web building fibers and combined with a filler. The filler can be present in an amount from about 1% to about 40% by weight. In an embodiment, the filler comprises calcium carbonate particles. In another embodiment, the filler comprises magnesium oxide particles. In another embodiment, the filler comprises a combination of calcium carbonate particles and magnesium oxide particles.

In an embodiment, the wrapping material can include an aerosol delivery composition applied to the wrapping material. The aerosol delivery composition contains an aerosol delivery agent. In an embodiment, the aerosol delivery agent comprises a drug or a flavorant. The aerosol delivery composition can be an oil, an aqueous solution, an aqueous dispersion, or a solid in any of the embodiments described herein. In an embodiment, the aerosol delivery agent comprises nicotine. In an embodiment, the aerosol delivery agent comprises a cannabinoid. In an embodiment, the aerosol delivery agent comprises tetrahydrocannabinol. In an embodiment, the aerosol delivery agent comprises cannabidiol. In an embodiment, the aerosol delivery agent comprises a combination of tetrahydrocannabinol and cannabidiol. Nicotine or a cannabinoid can also be combined with other aerosol delivery agents. In an embodiment, the other aerosol delivery agent is sugar. In an embodiment, the other aerosol delivery agent comprises a licorice extract. In an embodiment, the other aerosol delivery agent comprises honey. In an embodiment, the other aerosol delivery agent comprises coffee. In an embodiment, the other aerosol delivery agent comprises maple syrup. In an embodiment, the other aerosol delivery agent comprises a plant extract, such as a tea extract or a botanical extract. In an embodiment, the other aerosol generating agent comprises a tobacco extract. In embodiment, the aerosol delivery agent comprises a tobacco extract alone. In an embodiment, the aerosol delivery composition contains a terpene or a blend of terpenes. A terpene or a blend of terpenes can be used with any of the aerosol delivery agents described above including nicotine or a cannabinoid.

The aerosol delivery composition containing one or more aerosol delivery agents can be present in the wrapping material in an amount greater than about 1% by weight. In an embodiment, one or more aerosol delivery agents are present in an amount greater than about 3% by weight, such as in an amount greater than about 5% by weight. One or more aerosol delivery agents can be present on the wrapping material in any of the embodiments described above in an amount less than about 50% by weight, such as in an amount less than about 25% by weight.

In an embodiment, the web comprises extracted cocoa husk fibers combined with web building fibers and combined with water soluble cocoa husk components. The water soluble cocoa husk components can be present in an amount less than 10% by weight. In an alternative embodiment, the water soluble cocoa husk components can be present in an amount greater than about 10% by weight, such as greater than about 15% by weight, and less than about 50% by weight, such as less than about 30% by weight.

In an embodiment, the extracted cocoa husk fibers and the web building fibers are refined in an amount greater than about 60° SR, such as greater than about 75° SR, and generally less than about 95° SR.

In an embodiment, the wrapping material may include a web comprising extracted cocoa husk fibers, web building fibers, a tobacco material, and optionally a filler.

In any of the above embodiments, the wrapping material can include a plurality of discrete reduced ignition areas spaced along a first direction of the wrapping material. The reduced ignition areas can have a diffusivity of less than about 0.5 cm/s at 23° C.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. A wrapping material for a smoking article comprising:
a web comprising extracted cocoa husk fibers wherein at least a portion of water soluble components contained in the cocoa husk fibers have been removed via an aqueous solution, the extracted cocoa husk fibers combined with web building fibers, the web having a basis weight of from 20 gsm to 80 gsm and having a permeability of from 10 Coresta to 100 Coresta, and wherein the web has been treated with a gum.

2. A wrapping material as defined in claim 1, wherein the extracted cocoa husk fibers are combined with the web building fibers in a manner that produces a uniform speckled appearance over a surface of the wrapping material.

3. A wrapping material as defined in claim 1, wherein the web has a permeability of from 30 Coresta to 80 Coresta.

4. A wrapping material as defined in claim 1, wherein the web contains the web has a tensile strength of greater than 1000 cN/15 mm when tested according to ASTM Test D828-97.

5. A wrapping material as defined in claim 1, wherein the web has been calendared.

6. A wrapping material as defined in claim 1, wherein the extracted cocoa husk fibers and the web building fibers are refined in an amount greater than 75° SR and less than 90° SR, wherein ° SR stands for Schopper-Riegler.

7. A wrapping material as defined in claim 1, wherein the wrapping material is tobacco-free.

8. A wrapping material as defined in claim 1, wherein the gum comprises guar gum, alginate, carboxymethyl cellulose, or mixtures thereof.

9. A wrapping material as defined in claim 1, wherein the gum is present on the web in an amount of from 0.1% by weight to 5% by weight.

10. A wrapping material as defined in claim 1, wherein nicotine is present in the wrapping material in an amount of 0.5% or less by weight.

11. A wrapping material as defined in claim 1, wherein the web contains water soluble cocoa husk components in an amount greater than 10% by weight.

12. A wrapping material as defined in claim 1, further comprising an aerosol delivery composition applied to the web, the aerosol delivery composition containing an aerosol delivery agent.

13. A wrapping material as defined in claim 12, wherein the aerosol delivery agent comprises a cannabinoid.

14. A wrapping material as defined in claim 12, wherein the aerosol delivery agent comprises tetrahydrocannabinol.

15. A wrapping material as defined in claim 12, wherein the aerosol delivery agent comprises cannabidiol.

16. A wrapping material as defined in claim 12, wherein the aerosol delivery agent comprises a sugar, a licorice extract, honey, a coffee extract, maple syrup, a tea extract, a plant extract, a botanical extract, a tobacco extract, or a fruit extract.

17. A wrapping material as defined in claim 12, wherein the aerosol delivery composition contains a blend of terpenes.

18. A wrapping material for a smoking article comprising: a web comprising extracted cocoa husk fibers wherein at least a portion of water soluble components contained in the cocoa husk fibers have been removed via an aqueous solution, the extracted cocoa husk fibers combined with web building fibers, the web having a basis weight of from 20 gsm to 80 gsm and having a permeability of from 10 Coresta to 100 Coresta, and wherein the web has been treated with a humectant.

19. A wrapping material as defined in claim 18, wherein the humectant comprises glycerol, propylene glycol, or mixtures thereof.

20. A wrapping material as defined in claim 18, wherein the wrapping material has been further treated with a gum.

21. A wrapping material as defined in claim 18, further comprising an aerosol delivery composition applied to the web, the aerosol delivery composition containing an aerosol delivery agent.

22. A wrapping material as defined in claim 18, wherein the extracted cocoa husk fibers and the web building fibers are refined in an amount greater than 75° SR, and less than 90° SR.

* * * * *